United States Patent [19]

Graves, Jr. et al.

[11] Patent Number: 4,604,097

[45] Date of Patent: Aug. 5, 1986

[54] BIOABSORBABLE GLASS FIBERS FOR USE IN THE REINFORCEMENT OF BIOABSORBABLE POLYMERS FOR BONE FIXATION DEVICES AND ARTIFICIAL LIGAMENTS

[75] Inventors: George A. Graves, Jr., Bellbrook; Binod Kumar, Centerville, both of Ohio

[73] Assignee: University of Dayton, Dayton, Ohio

[21] Appl. No.: 702,526

[22] Filed: Feb. 19, 1985

[51] Int. Cl.$^4$ .................. C04B 33/24; C04B 35/44
[52] U.S. Cl. ........................ 623/11; 623/16; 623/18; 433/201.1; 501/35; 501/45; 106/35
[58] Field of Search ............... 3/1.9, 1, 1.91; 433/201

[56] References Cited

U.S. PATENT DOCUMENTS

| | | | |
|---|---|---|---|
| 4,155,124 | 5/1979 | Kawahara et al. | 3/1.9 |
| 4,218,355 | 8/1980 | Bajpai et al. | 106/45 |
| 4,308,064 | 12/1981 | Takami et al. | 128/92 C |

OTHER PUBLICATIONS

IADR Abstracts 1982, "Strengthening Biodegradable Polymers for Bone Fixation and Support," R. L. Dunn et al.

Casper et al., "Totally Biodegradable Fracture-Fixation Plates for Use in Maxillofacial Surgery," Second World Congress on Biomaterials, 10th Annual Meeting of the Society for Biomaterials, Washington, D.C., Apr. 27–May 1, 1984.

*Primary Examiner*—John Kight
*Assistant Examiner*—M. L. Moore
*Attorney, Agent, or Firm*—Biebel, French & Nauman

[57] ABSTRACT

A spun or drawn glass fiber for use in the area of medical implants, and particularly as a reinforcement for bioabsorbable polymeric orthopaedic and dental implants. The glass fiber is bioabsorbable and has sufficient tensile strength and elasticity to be used as a reinforcement. It is made up of 5–50% calcium oxide (CaO), 50–95% phosphorous pentoxide ($P_2O_5$), 0–5% calcium fluoride ($CaF_2$), 0–5% water ($H_2O$), and 0–10% XO wherein X is either a single magnesium, zinc or strontium ion or two sodium, potassium, lithium, or aluminum ions and when X is aluminum the O represents three oxygen ions.

15 Claims, No Drawings

BIOABSORBABLE GLASS FIBERS FOR USE IN THE REINFORCEMENT OF BIOABSORBABLE POLYMERS FOR BONE FIXATION DEVICES AND ARTIFICIAL LIGAMENTS

BACKGROUND OF THE INVENTION

The present invention relates to biocompatible and bioabsorbable glass fibers for use in the area of medical implants, particularly orthopaedic and dental implants. More particularly, it relates to spun or drawn fibers containing primarily calcium oxide (CaO) and phosphorous pentoxide ($P_2O_5$) which may be used as a reinforcement for resorbable polymeric bone plates and artificial ligaments.

Many different materials have been used in the area of orthopaedic and dental implant devices. For example, various metals have been used as internal fixation devices, the most common being compression plates, rods or pins. Today the vast majority of these devices are made up of stainless steel or titanium. They are used to hold fractured pieces of long bones in correct alignment and to minimize movement until a satisfactory union can take place by natural bone fracture healing processes.

This technique can provide quite satisfactory results; however, several problems can occur due to large differences in the modulus of elasticity of the bone and metal which usually results in the need for a second operation to remove the device. Also, for reasons not completely understood, some individuals do not tolerate the metal and the bone, or surrounding soft tissue, has an inflammatory response to the metal.

The problem of differing elastic modulus between the bone and metal plate and the need for a second operation can be, in some instances, directly related. In many cases, the person receiving the implant does not have the implant removed, either due to their own neglect or the surgeons. Even if a satisfactory bone union takes place, the large difference in the strength and modulus will actually result in a deterioration of the bone in the vicinity of the metal plate. If the condition is allowed to persist, severe pain and/or refracturing of the bone can occur. Also, if the plate is removed, the underlying healed bone (callus) is usually not well organized. That is, the composite structure of the bone has not aligned itself such that it has maximum strength along the direction (axis) of highest stress, which is the natural behavior of healthy mature bone. This can best take place if the stresses placed upon the bone are gradual, allowing the bone sufficient time to reorganize.

A similar problem exists in the attempted repair of torn, or partially torn ligaments or tendons. Ligaments are composed of interwoven strands of collagen fibers very much like hemp rope. When these fibers are broken, they will, if properly stabilized and the blood supply is adequate, repair themselves. In a manner similar to bone, the collagen fibers do not realign themselves along lines of maximum stress if the stresses are being distributed over a permanently placed artificial support, such as metal wires. They remain in a disorganized mass, like scar tissue, with a much reduced strength when compared to normal ligamentous material. If the supporting artificial material is surgically removed, if that is even possible, there is great danger of the patient suddenly applying stress to the ligament that is too high for it to withstand and further damage will occur.

For this reason, it has been proposed that a biocompatible composition be used in the repair or replacement of human body parts such as ligaments, tendons and bones. Thus, Alexander et al. in U.S. Pat. Nos. 4,329,743 and 4,411,027 disclose using a composite of a bioabsorbable polymer (polylactic acid) on a substrate of a plurality of carbon fibers. See also U.S. Pat. Nos. 4,141,087, 4,140,678 and 4,052,988 which diclose various bioabsorbable synthetic polymers for use as permanent sutures, artificial ligaments and bone plates. However, while the polymer of Alexander et al. is bioabsorbable, the carbon fiber reinforcement is not. Since 30-60% of the bone plates and artificial ligaments of Alexander et al. are made up of the carbon fibers, the problem of bioincompatibility remains due to their being stiff and non-bioabsorbable.

It is also known that bioabsorbable ceramic materials may be used as medical implants. See, for example, U.S. Pat. No. 4,218,355 (assigned to the same assignee as the present invention), which discloses use of an aluminum oxide/calcium oxide/phosphorous pentoxide porous ceramic material as a carrier for controlled release of proteins, polypeptide hormones and other substances. It is also known that this type of ceramic composition may be used as a bioabsorbable bone graft material. See also, U.S. Pat. No. 4,155,124, which discloses a burnt ceramic bone implant, and the IADR Abstracts in the March 1982 issue of the *Journal of Dental Research,* various ones of which disclose work with biodegradable ceramic materials.

Despite the recent efforts to develop a bioabsorbable composition or composite which may be used as an orthopaedic and dental implant, much work remains to be done. The bioabsorbable synthetic polymers do not by themselves have sufficient structural strength to be used alone as an implant and the porous ceramic materials tend to be too rigid and brittle. Accordingly, the need exists for an improved biocompatible and bioabsorbable material for use in the area of orthopaedic and dental implants, and particularly a material which can be used to reinforce existing bioabsorbable synthetic polymers to form a composite suitable for that purpose.

SUMMARY OF THE INVENTION

The present invention meets that need by providing a reinforcement for bioabsorbable polymeric orthopaedic and dental implants, such a bone plates and artificial ligaments. The reinforcement is a spun or drawn glass fiber having the required tensile strength and resorption properties. As such, the glass fiber is able to reinforce a polymer matrix as the resorbable polymer and the glass fiber is gradually being reduced in strength and elastic modulus (through slow, steady bioabsorption), while allowing the bone or ligament to gradually reorganize and increase to normal strength and modulus. After a resonable period of time (approximately one year), the implant, including the glass fiber reinforcement, is completely consumed in the body causing no inflammatory, carcinogenic, or toxic reactions. This is because of the bioabsorbable nature of the glass fiber reinforcement.

The spun or drawn glass fiber of the present invention is basically made up of a binary mixture of calcium oxide (CaO) and phosphorous pentoxide ($P_2O_5$); although, other ingredients such as calcium fluoride ($CaF_2$), water ($H_2O$), and other oxides containing cations such as magnesium, zinc, strontium, sodium, potassium, lithium and aluminum may also be incorporated in small amounts. In terms of the binary mixture, the preferred Ca:P mole ratio is 0.25 to 0.33. Preferably, the glass comprises by weight 5-50% CaO, 50-95% $P_2O_5$, 0-5% $CaF_2$, 0-5% $H_2O$, and 0-10% XO, wherein X is a single magnesium, zinc or strontium ion or two sodium, potassium, lithium or aluminum ions and O is a single oxygen ion except when X is aluminum, in which case it is three oxygen ions. More preferably, the calcium oxide (CaO) is present by weight in the amount of 15-25%; the phosphorous pentoxide ($P_2O_5$) is present by weight in the amount of 65-90%; and either calcium fluoride ($CaF_2$) or water ($H_2O$) is present by weight in the amount of 0.1-4%.

The glass composition which is spun or drawn into the glass fiber reinforcement should obviously have good melting and fiber drawing characteristics. It should be capable of being drawn into fibers having a diameter between 1 to 100 microns, preferably 5 to 25 microns, and most preferably 8 to 15 microns, without crystallization during fiber drawing. Likewise, the drawn fibers should have a good tensile strength and modulus of elasticity.

Finally, the drawn fiber should be bioabsorbable, i.e., it should dissolve in vitro in a static solution of buffered saline in approximately 30 to 40 days, and should absorb in vivo, as implanted, slowly over six months to one year. In this manner, the glass fiber reinforcement of the present invention is able to gradually loose strength and safely absorb in the body as the strength of the bone, ligament, tendon or other body part is gradually and effectively increased. The glass fiber of the present invention, appropriately coated with a thin protective coating, may also be used by itself (and not necessarily as a reinforcement) as a bioabsorbable suture, lashing, or other type of medical implant.

Accordingly, it is an object of the present invention to provide a spun or drawn glass fiber which is bioabsorbable and useful in the area of medical implants, particularly orthopaedic and dental implants.

These and other objects of the invention will be apparent from the following description and the appended claims.

DETAILED DESCRIPTION OF THE PREFERRED EMBODIMENTS

The glass composition used to produce the glass fiber reinforcement of the present invention as mentioned, preferably contains by weight 5-50%, most preferably 15-25%, calcium oxide (CaO) and 50-95%, most preferably 65-90%, phosphorous pentoxide ($P_2O_5$). The preferred atomic ratio for calcium:phosphorous is about 0.25 to 0.33. Thus, in its basic form, the glass composition is a binary mixture of calcium oxide and phosphorous pentoxide in the given ranges and having the preferred Ca:P mole ratio. However, usually other constituents are also present. It may contain from 0-5% and preferably 0.1-4% by weight calcium fluoride ($CaF_2$) or water ($H_2O$) or one or more of other oxides such as magnesium oxide (MgO), zinc oxide (ZnO), strontium oxide (SrO), sodium oxide ($Na_2O$), potassium oxide ($K_2O$), or lithium oxide ($Li_2O$), or aluminum oxide ($Al_2O_3$).

It is important, however, that any added fluoride or oxide not result in development of undue crystallinity in the glass composition during fiber drawing. That is, the glass composition must be readily melted to a homogeneous liquid having melt viscosity suitable for fiber drawing purposes. Typically, these compositions have a melt viscosity of about 1000 to 10,000 poise at the drawing temperature. The drawing temperature is preferably at least about 100° C. above the liquidus temperature of the composition. It should be capable of being spun or drawn to a diameter of between 1 to 100 microns, preferably between 5 to 25 microns, and most preferably 8 to 15 microns using ordinary techniques. And it should have good tensile strength and modulus of elasticity so as to not be too rigid and brittle as are many ceramic materials.

In terms of tensile strength, the fiber should have a tensile strength ranging from 200 to 550 megapascals (MPa) and 30 to 200 thousand pounds per square inch (Ksi), i.e., 30,000 to 80,000 psi. The preferred range for Young's modulus is $2 \times 10^6$ to $7 \times 10^6$ psi.

Also as mentioned, the fiber should be bioabsorbable so that upon implanting it will gradually resorb over a six-month to one-year period. A key to this is the fact that the chemical composition of the glass reinforcement fibers of the present invention is similar to that of fluoro and hydroxy apatite minerals which closely resemble the chemistry of bone materials. The chemical formulas for the fluoro and hydroxy apatites are $Ca_{10}P_6O_{24}F_2$ and $Ca_{10}P_6O_{24}(OH)_2$, respectively. If these formulas are expressed as oxide and fluoride weight percent, the fluoro apatite would be expressed as CaO—50.01%, $CaF_2$—7.74%, and $P_2O_5$—42.25%. Similarly, the hydroxy apatite would be expressed as CaO—54.91%, $H_2O$—3.33%, and $P_2O_5$—41.75%. These two minerals in the crystalline state can be chemically synthesized in the laboratory. These chemically synthesized apatites in powder or aggregate form are available in the market for bio-applications.

For present purposes, a material in the fibrous form is, however, being sought. The fabrication of fibers from the two crystalline apatite minerals is difficult and to our knowledge has not before been used to produce a glass fiber reinforcement for use in the area of medical implants. However, if these two minerals can be produced in the vitreous or amorphous state and a desirable viscosity range is obtained, fibers could easily be drawn. The present invention relates to the development of glass compositions for fiber making from the CaO—$CaF_2$—$P_2O_5$ and CaO—$H_2O$—$P_2O_5$ system.

EXAMPLE I

Analytical grade powders of CaO, $CaF_2$, and $P_2O_5$ were weighed to obtain a predetermined ratio and were then thoroughly mixed. The mixed batches were melted in a platinum crucible. The melting temperature and time depended upon the composition. The melting temperature ranged from 800° C. to 1400° C., and the melting time varied from 15 minutes to 6 hours. The objective in all the melting experiments was to obtain a clear and homogeneous melt from which fibers could be drawn. After melting, the crucible was transferred to another furnace which was maintained at a lower temperature in order to maintain a proper viscosity for fiber drawing. The fibers were then drawn manually and the suitability of the various melts for fiber drawing was evaluated. The results are set forth in Table I.

TABLE I

| COMPOSITIONS IN WEIGHT PERCENT | | | | |
|---|---|---|---|---|
| Compositions: | #1 | #2 | #3 | #4 |
| CaO | 50.01 | 48.00 | 40.00 | 23.00 |
| $CaF_2$ | 7.74 | 7.75 | 6.00 | 0.00 |

TABLE I-continued

| COMPOSITIONS IN WEIGHT PERCENT | | | | |
|---|---|---|---|---|
| Compositions: | #1 | #2 | #3 | #4 |
| $P_2O_5$ | 42.25 | 44.25 | 54.00 | 77.00 |

Remarks:
Composition #1: Highly refractory composition. Melting at 1400° C. produced insignificant amount of liquid or glass phase.
Composition #2: Melted at 1400° C. A clear and homogeneous liquid was produced. However, fibers would not be drawn; the glass crystallized spontaneously during fiber drawing.
Composition #3: The composition melted to a homogeneous and clear liquid. Improved melt viscosity, but still crystallized during fiber drawing.
Composition #4: Melted at 900° C. Clear and homogeneous glass obtained. The composition exhibited excellent properties for fiber drawing.

As can be seen from Table I, composition #1 corresponds to the fluoro apatite mineral. This composition is highly refractory and difficult to melt. By reducing CaO and increasing $P_2O_5$ contents, the meltability was improved as in composition #2; however, it crystallized during fiber drawing. By further decreasing CaO and $CaF_2$, and increasing $P_2O_5$ as in compositions #3 and #4, meltability as well as fiber drawing characteristics were improved. Composition #4 exhibited the most desirable melting and fiber drawing characteristics. Several hundred grams of glass and fibers were produced from composition #4 for use in biocompatibility evaluations.

Glass fibers drawn from composition #4 were drawn to diameters ranging from 0.0024–0.0045 inches. Some of these were tested for tensile strength and elasticity. The average tensile strength (five fibers tested) was 37,100 psi. The average Young's modulus was $2.4 \times 10^6$ psi.

Some of the fibers drawn from composition #4 were placed in a static solution of buffered saline and were found to go into solution after approximately 40 days. Others of the fibers drawn from composition were implanted in rats and rabbits as single fibers and as fibers coated with a solution of polylactic acid. The results after 4, 12 and 24 week implant periods showed that the fibers slowly degraded and were consumed in the physiological environment, causing no inflammation or other untoward effects that could be ascertained by standard histological examination.

EXAMPLE II

Eighty-five (85) grams of bulk glass was prepared from, by weight, 20% calcium oxide (CaO), 77% phosphorous pentoxide ($P_2O_5$), and 3% water ($H_2O$). The entire 85 grams was drawn into a continuous fiber that ranged in diameter from 8 to 12 microns.

Static dissolution studies performed on some of the fibers showed them to be absorbable in vitro (in buffered saline) and others of fibers from the same batch were implanted (uncoated) in the back muscles of rabbits. The histology indicated that these fibers dissolved in vivo and were consumed in approximately 6 months.

Others of the fibers were tested for mechanical properties. The results of those studies are set forth in Table II. As shown in Table II, ultimate tensile strength was determined from twenty-two mounted test fibers. A total of twenty-six fibers were mounted on 35 mm slide mounts using the technique discussed above. The diameter of each mounted fiber was determined by direct measurement on a micro-hardness tester. Specimens #4 and #26 were observed to be twisted double fiber mounts while measuring fiber diameters and therefore were not tested. Specimen #1 was broken during the cutting and clipping of the slide mount immediately prior to testing. Specimen #24 failed in the wax at the slide mount and was deemed an invalid test. The results for the remaining test specimens are compiled in Table II.

TABLE II

| GLASS FIBER TENSILE TEST RESULTS | | |
|---|---|---|
| SPECIMEN NUMBER | DIAMETER (microns) | ULTIMATE TENSILE STRENGTH |
| | | MPa | ksi |
| 2 | 12.3 | 362.4 | 52.6 |
| 3 | 11.2 | 402.3 | 58.3 |
| 5 | 14.1 | 317.9 | 46.1 |
| 6 | 13.6 | 357.9 | 51.9 |
| 7 | 12.0 | 376.4 | 54.6 |
| 8 | 13.1 | 414.9 | 60.2 |
| 9 | 12.4 | 320.9 | 46.5 |
| 10 | 12.6 | 360.3 | 52.3 |
| 11 | 13.6 | 393.8 | 42.6 |
| 12 | 11.6 | 339.7 | 49.3 |
| 13 | 12.5 | 372.5 | 54.0 |
| 14 | 12.8 | 301.9 | 43.8 |
| 15 | 10.8 | 463.7 | 67.2 |
| 16 | 11.1 | 472.5 | 68.5 |
| 17 | 12.8 | 521.5 | 75.6 |
| 18 | 13.2 | 414.3 | 60.1 |
| 19 | 11.5 | 410.8 | 59.6 |
| 20 | 12.0 | 459.7 | 66.7 |
| 21 | 11.2 | 450.1 | 65.3 |
| 22 | 10.7 | 512.8 | 74.4 |
| 23 | 13.2 | 448.0 | 65.0 |
| 25 | 13.5 | 390.6 | 56.7 |
| $\bar{x}$ | 12.4 | 398.4 | 57.8 |
| s | 1.0 | 65.2 | 9.5 |

While the product herein described constitutes preferred embodiments of the invention, it is to be understood that the invention is not limited to this precise product, and that changes may be made therein without departing from the scope of the invention which is defined in the appended claims.

What is claimed is:

1. A spun or drawn glass fiber, which is bioabsorbable and useful in the area of medical implants, comprising calcium oxide (CaO) and phosphrous pentoxide ($P_2O_5$).

2. The glass fiber of claim 1 wherein said fiber has a diameter in the range of 1-100 microns.

3. The glass fiber of claim 2 wherein said fiber has a diameter in the range of 5-25 microns.

4. The glass fiber of claim 2 wherein said glass fiber comprises by weight:

| CaO | 5-50% |
|---|---|
| $P_2O_5$ | 50-95% |
| $CaF_2$ | 0-5% |
| $H_2O$ | 0-5% |
| XO | 0-10% | wherein X is selected from the group consisting of a single magnesium, zinc or strontium ion and two sodium, potassium, lithium or aluminum ions, and when X is aluminum O is three oxygen ions.

5. The glass fiber of claim 4 wherein said calcium oxide (CaO) is present by weight in the amount of 15-25% and said phosphorous pentoxide ($P_2O_5$) is present by weight in the amount of 65-90%.

6. The glass fiber of claim 4 wherein said calcium fluoride ($CaF_2$) is present by weight in the amount of 0.1-4%.

7. The glass fiber of claim 4 wherein said water ($H_2O$) is present by weight in the amount of 0.1-4%.

8. The glass fiber of claim 1 wherein the Ca:P atomic ratio is about 0.25 to 0.33.

9. A reinforcement for a bioabsorbable polymeric orthopaedic or dental implant comprising a drawn or spun glass fiber made up of by weight of:

|  |  |
|---|---|
| CaO | 5–50% |
| $P_2O_5$ | 50–95% |
| $CaF_2$ | 0–5% |
| $H_2O$ | 0–5% |
| XO | 0–10% | wherein X is selected from the group consisting of a single magnesium, zinc or strontium ion and two sodium, potassium, lithium or aluminum ions, and when X is aluminum O is three oxygen ions.

10. The reinforcement of claim 9 wherein said fiber has a diameter in the range of 5 to 25 microns.

11. The reinforcement of claim 10 wherein said fiber has a diameter in the range of 8 to 15 microns.

12. The reinforcement of claim 11 wherein said fiber has a tensile strength of 30,000 to 200,000 psi and a Young's modulus of $2 \times 10^6$ to $7 \times 10^6$ psi.

13. The reinforcement of claim 12 wherein said glass fiber comprises by weight:

|  |  |
|---|---|
| CaO | 15–25%, |
| $P_2O_5$ | 65–90%, and |
| $H_2O$ | 0.1–4% |

14. The reinforcement of claim 9 wherein the Ca:P atomic ratio is 0.25 to 0.33.

15. The glass fiber of claim 1 wherein said fiber has a melt viscosity of 1000 to 10,000 poise at its drawing temperature.

* * * * *

REEXAMINATION CERTIFICATE (1549th)
United States Patent [19]
Graves, Jr. et al.

[11] B1 4,604,097
[45] Certificate Issued Sep. 10, 1991

[54] BIOABSORBABLE GLASS FIBERS FOR USE IN THE REINFORCEMENT OF BIOABSORBABLE POLYMERS FOR BONE FIXATION DEVICES AND ARTIFICIAL LIGAMENTS

[75] Inventors: George A. Graves, Jr., Bellbrook; Binod Kumar, Centerville, both of Ohio

[73] Assignee: University of Dayton, Dayton, Ohio

Reexamination Request:
No. 90/002,217, Dec. 5, 1990

Reexamination Certificate for:
Patent No.: 4,604,097
Issued: Aug. 5, 1986
Appl. No.: 702,526
Filed: Feb. 19, 1985

[51] Int. Cl.$^5$ .................. C04B 33/24; C04B 35/44
[52] U.S. Cl. ........................... 623/11; 623/16; 623/18; 433/201.1; 501/35; 501/45; 106/35
[58] Field of Search ................... 623/11, 16, 18; 433/201.1; 501/35, 45; 106/35

[56] References Cited

U.S. PATENT DOCUMENTS

| | | | |
|---|---|---|---|
| 4,052,988 | 10/1977 | Doddi et al. | 128/335.5 |
| 4,140,678 | 2/1979 | Shalaby et al. | 260/860 |
| 4,141,087 | 2/1979 | Shalaby et al. | 623/11 |
| 4,192,021 | 3/1980 | Deibig et al. | 623/11 |
| 4,279,249 | 7/1981 | Vert et al. | 128/92 |
| 4,329,743 | 5/1982 | Alexander et al. | 623/11 |
| 4,350,675 | 9/1982 | Drake | 424/1 |
| 4,360,625 | 11/1982 | Griffith | 524/414 |
| 4,411,027 | 10/1983 | Alexander et al. | 623/11 |
| 4,612,923 | 9/1986 | Kronenthal | 128/92 |
| 4,613,577 | 9/1986 | Tagai et al. | 501/35 |

FOREIGN PATENT DOCUMENTS

| | | |
|---|---|---|
| 135053 | 8/1984 | Japan. |
| 1593288 | 7/1981 | United Kingdom. |
| 2099702 | 12/1982 | United Kingdom. |
| 2142914 | 1/1985 | United Kingdom. |

OTHER PUBLICATIONS

Biodegradable Composite Materials for Bone Surgery, J. L. Leray et al, p. 70, 3rd Annual Meeting of the Society for Biomaterials; 9th Annual International Biomaterials Symposium, New Orleans, LA; Hyatt Regency Hotel.

Ceramics, Glasses, and Composites in Medicine, L. L. Hench, Ph.D., Medical Instrumentation, vol. 7, No. 2, Mar.-Apr. 1973.

Controlled Release Glasses (C.R.G.) for Biomedical Uses, J. Burnie et al, Biomaterials 1981, vol. 2, Oct.

Development of Biodegradable Implants for Use in Maxillofacial Surgery, Southern Research Institute, Aug. 1979; Jun. 1982; Oct. 1981.

Abstracts, "The Processing of Bioceramics", L. L. Hench.

*Primary Examiner*—John Kight, III

[57] ABSTRACT

A spun or drawn glass fiber for use in the area of medical implants, and particularly as a reinforcement for bioabsorbable polymeric orthopaedic and dental implants. The glass fiber is bioabsorbable and has sufficient tensile strength and elasticity to be used as a reinforcement. It is made up of 5–50% calcium oxide (CaO), 50–95% phosphorous pentoxide ($P_2O_5$), 0–5% calcium fluoride ($CaF_2$), 0–5% water ($H_2O$), and 0–10% XO wherein X is either a single magnesium, zinc or strontium ion or two sodium, potassium, lithium, or aluminum ions and when X is aluminum the O represents three oxygen ions.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4, 5, 9 and 13 are cancelled.

Claims 3, 6, 7, 8, 10, 14, 15 are determined to be patentable as amended.

Claims 11 and 12, dependent on an amended claim, are determined to be patentable.

New claims 16 and 17 are added and determined to be patentable.

3. The glass fiber of claim [2] *16* wherein said fiber has a diameter in the range of 5-25 microns.

6. The glass fiber of claim [4] *16* wherein said calcium fluoride ($CaF_2$) is present by weight in the amount of 0.1-4%.

7. The glass fiber of claim [4] *16* wherein said water ($H_2O$) is present by weight in the amount of 0.1-4%.

8. The glass fiber of claim [1] *16* wherein the Ca:P atomic ratio is about 0.25 to 0.33.

10. The reinforcement of claim [9] *17* wherein said fiber has a diameter in the range of 5 to 25 microns.

14. The reinforcement of claim [9] *17* wherein the Ca:P atomic ratio is 0.25 to 0.33.

15. The glass fiber of claim [1] *16* wherein said fiber has a melt viscosity of 1000 to 10,000 poise at its drawing temperature.

*16. A spun or drawn glass fiber having a diameter in the range of 1-100 microns, which is bioabsorbable and useful in the area of medical implants, comprising by weight*

| | |
|---|---|
| CaO | 15-25% |
| $P_2O_5$ | 65-90% |
| $CaF_2$ | 0-5% |
| $H_2O$ | 0-5% |
| XO | 0-10% |

*wherein X is selected from the group consisting of a single magnesium, zinc, or strontium ion and two sodium, potassium, lithium, or aluminum ions, and when X is aluminum, O is three oxygen ions.*

*17. A reinforcement for a bioabsorbable polymeric orthopaedic or dental implant comprising a drawn or spun glass fiber having a diameter in the range of 1-100 microns made up by weight of*

| | |
|---|---|
| CaO | 15-25% |
| $P_2O_5$ | 65-90% |
| $CaF_2$ | 0-5% |
| $H_2O$ | 0-5% |
| XO | 0-10% |

*wherein X is selected from the group consisting of a single magnesium, zinc, or strontium ion and two sodium, potassium, lithium, or aluminum ions, and when X is aluminum, O is three oxygen ions.*

* * * * *